United States Patent
Russell

(10) Patent No.: US 9,186,453 B1
(45) Date of Patent: Nov. 17, 2015

(54) SELF-RETRACTING HANG TAB

(75) Inventor: Paul Grady Russell, Campbell, CA (US)

(73) Assignee: Amazon Technologies, Inc., Reno, NV (US)

(*) Notice: Subject to any disclaimer, the term of this patent is extended or adjusted under 35 U.S.C. 154(b) by 49 days.

(21) Appl. No.: 13/589,888

(22) Filed: Aug. 20, 2012

(51) Int. Cl.
 A47G 29/00 (2006.01)
 A61M 5/14 (2006.01)

(52) U.S. Cl.
 CPC ................................. A61M 5/1414 (2013.01)

(58) Field of Classification Search
 CPC .. B65D 75/56; B65D 5/4208; B65D 73/0064; B65D 73/0071; B65D 25/22; A47G 1/1626
 USPC ............. 248/224.8, 214, 317, 489, 685, 307, 248/304, 339, 475.1, 478; 229/117.22; 206/166, 163, 806, 461, 349; 40/748, 40/759, 757, 606.01, 673; 211/118, 211/119.004, 85, 195
 See application file for complete search history.

(56) References Cited

U.S. PATENT DOCUMENTS

| | | | | |
|---|---|---|---|---|
| 2,609,137 | A * | 9/1952 | Toensmeier | 206/166 |
| 3,258,152 | A * | 6/1966 | Cameron | 206/166 |
| 4,403,690 | A * | 9/1983 | Fischer | 206/163 |
| 4,632,242 | A * | 12/1986 | Choi et al. | 206/45.24 |
| 5,328,137 | A * | 7/1994 | Miller et al. | 248/220.21 |
| 6,145,659 | A * | 11/2000 | Faircloth et al. | 206/292 |
| 6,305,597 | B1 * | 10/2001 | Donegan et al. | 229/117.22 |
| 6,609,693 | B2 * | 8/2003 | Hui | 248/489 |
| 6,769,541 | B1 * | 8/2004 | Carriere | 206/348 |
| 8,238,118 | B2 * | 8/2012 | Li et al. | 361/807 |
| 2009/0014610 | A1* | 1/2009 | Denola | 248/214 |
| 2011/0096523 | A1* | 4/2011 | Li et al. | 361/807 |

* cited by examiner

Primary Examiner — Terrell McKinnon
Assistant Examiner — Ingrid M Weinhold
(74) Attorney, Agent, or Firm — Lowenstein Sandler LLP

(57) ABSTRACT

Self-retracting hang tabs for product packages are described. Methods of manufacturing the self-retracting hang tabs are also described. One apparatus includes a frame to house a hang tab, the frame to be at least partially coupled to a surface of a product package, and the hang tab to allow the product package to be hung from a medium when in a deployed position. The apparatus also include a biasing member coupled to the frame and the hang tab, the biasing member to move the hang tab from the deployed position to a retracted position when not under tension. The biasing member is also configured to position the hang tab in a deployed position when the hang tab is under tension.

12 Claims, 11 Drawing Sheets

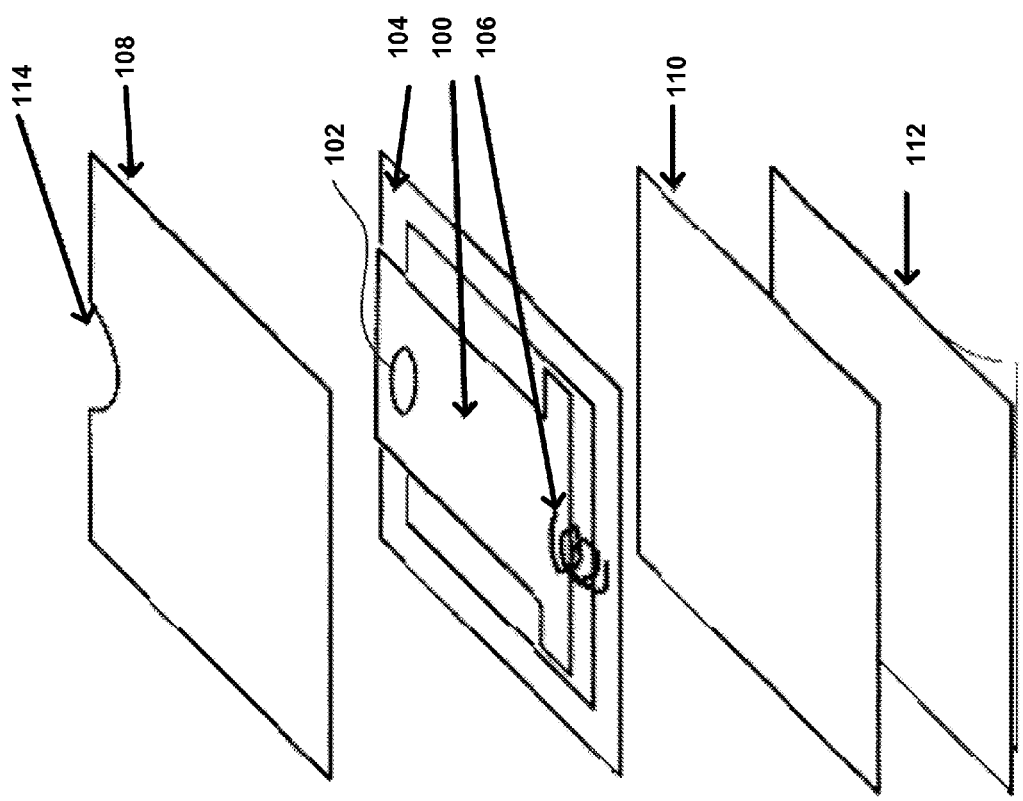

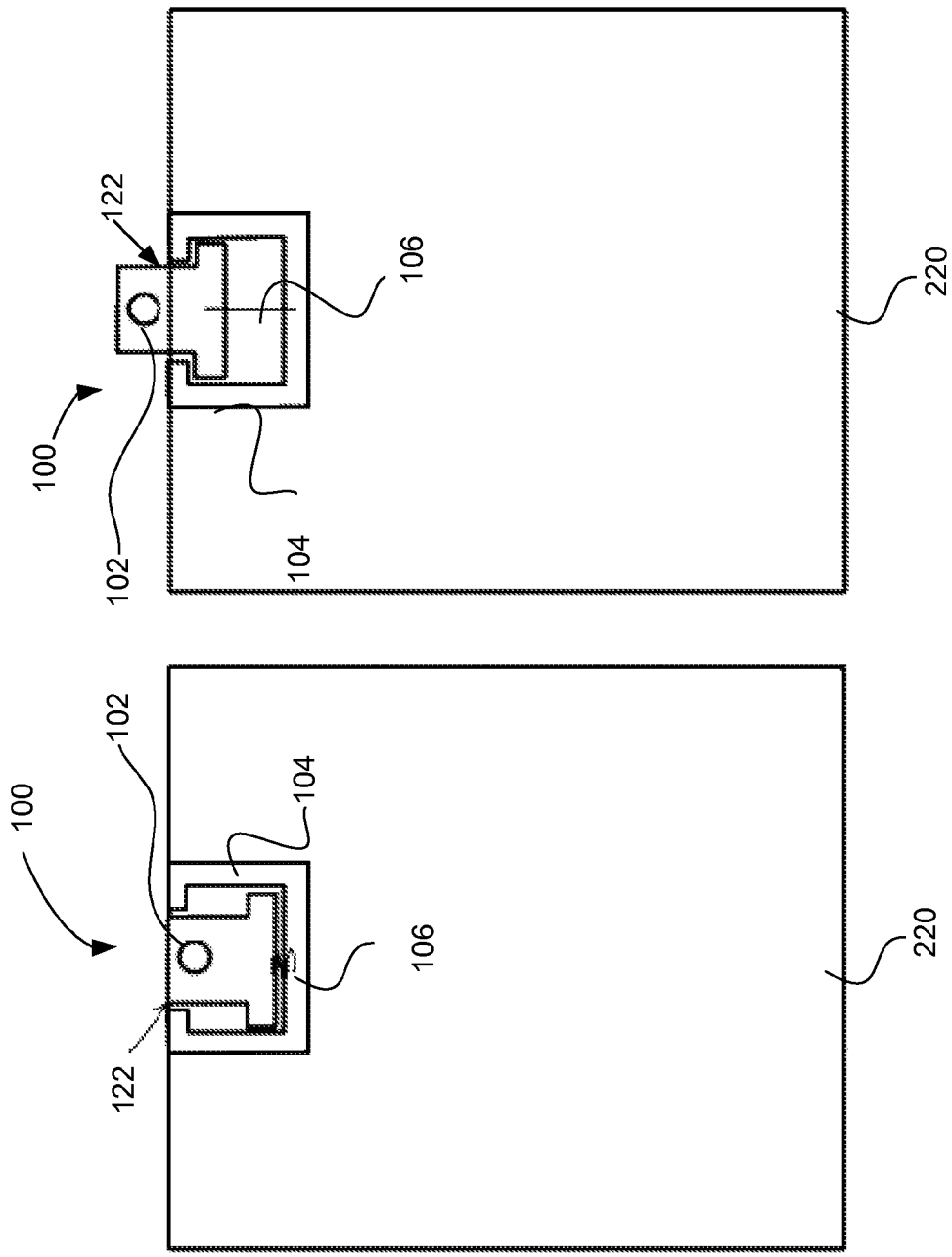

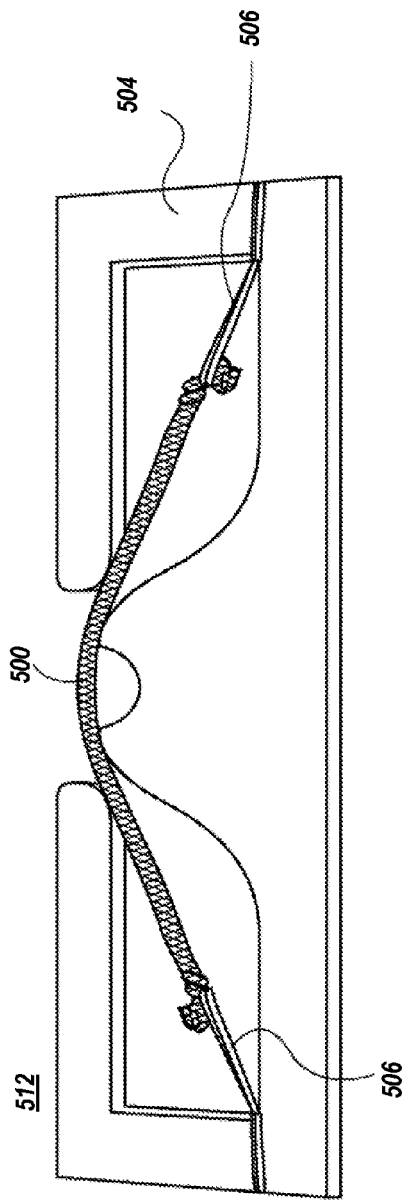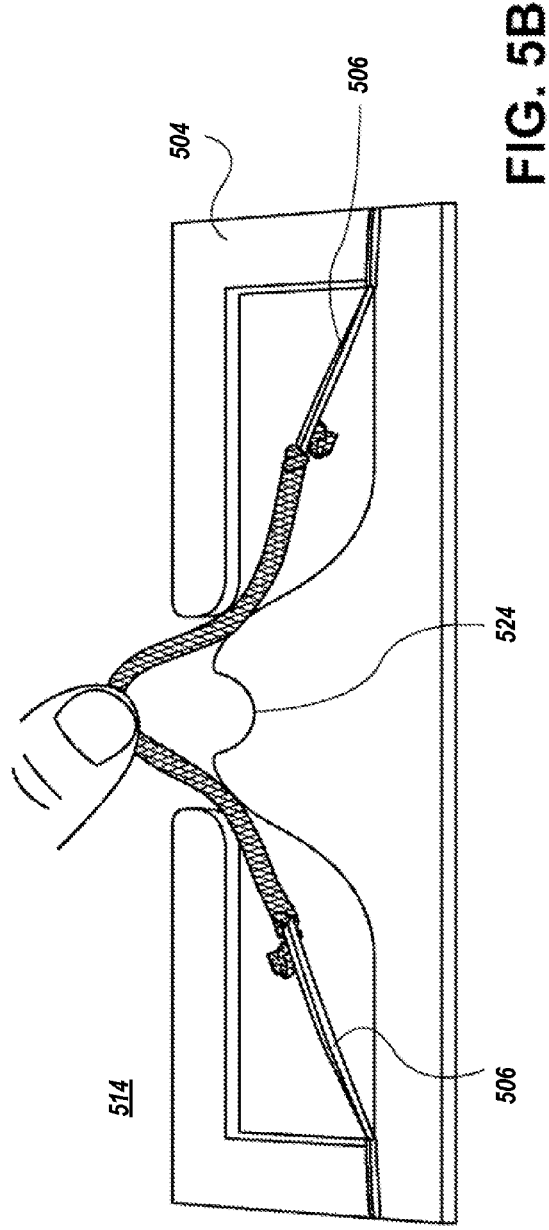

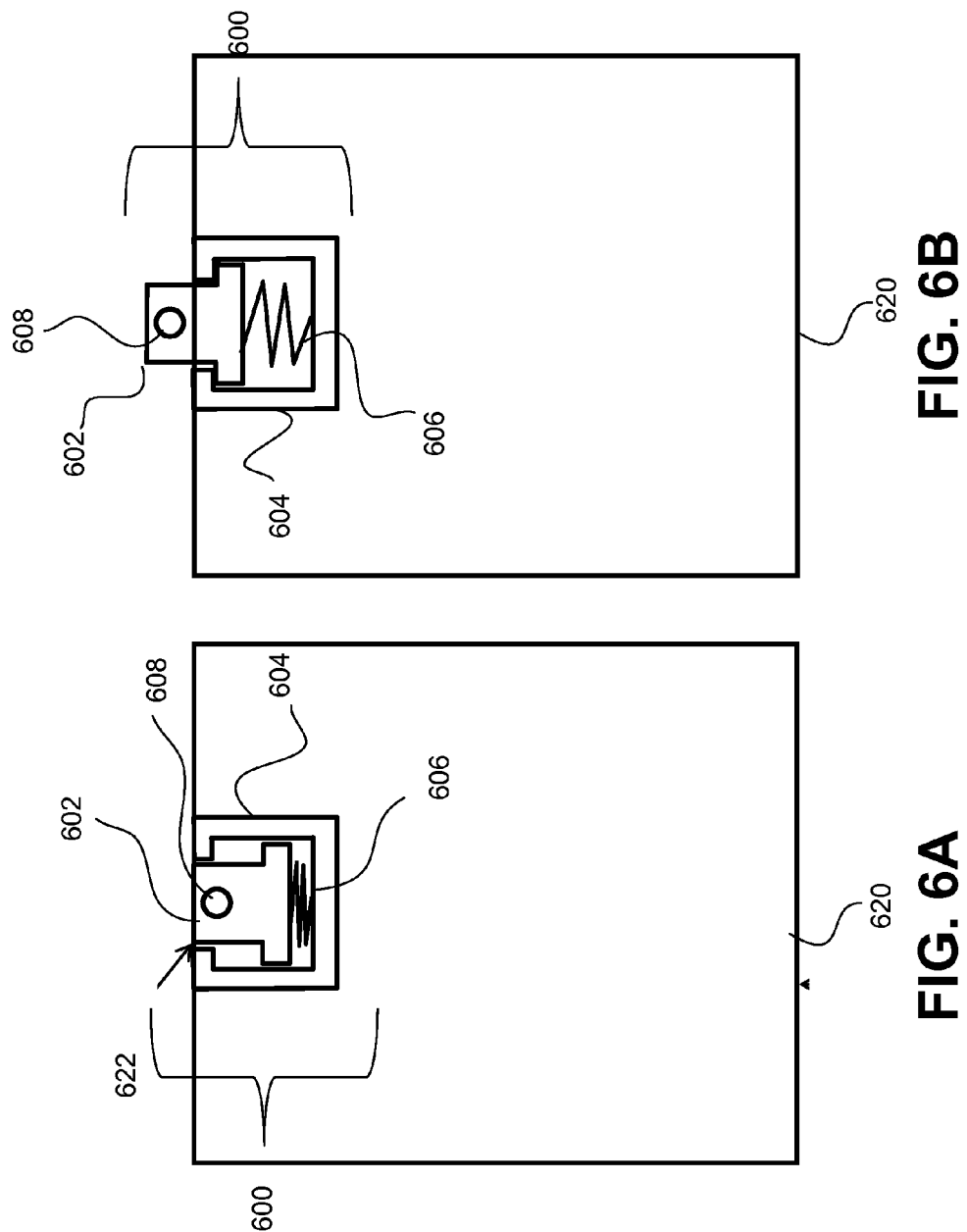

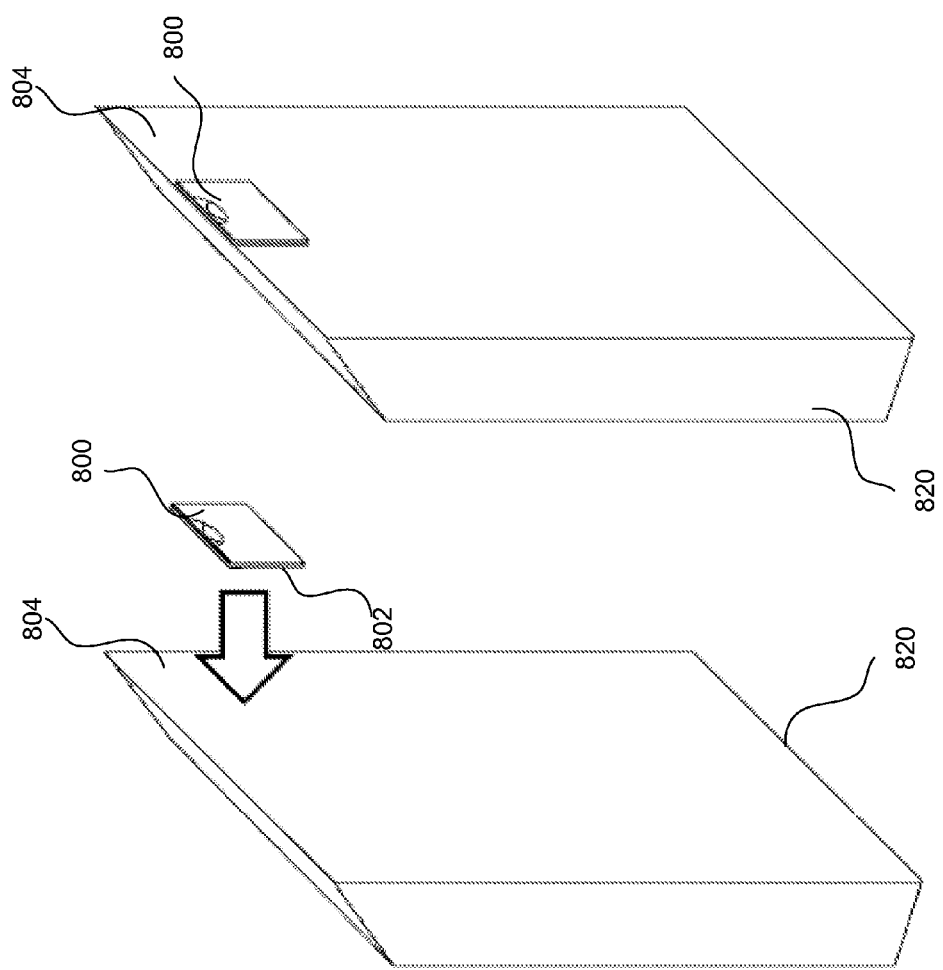

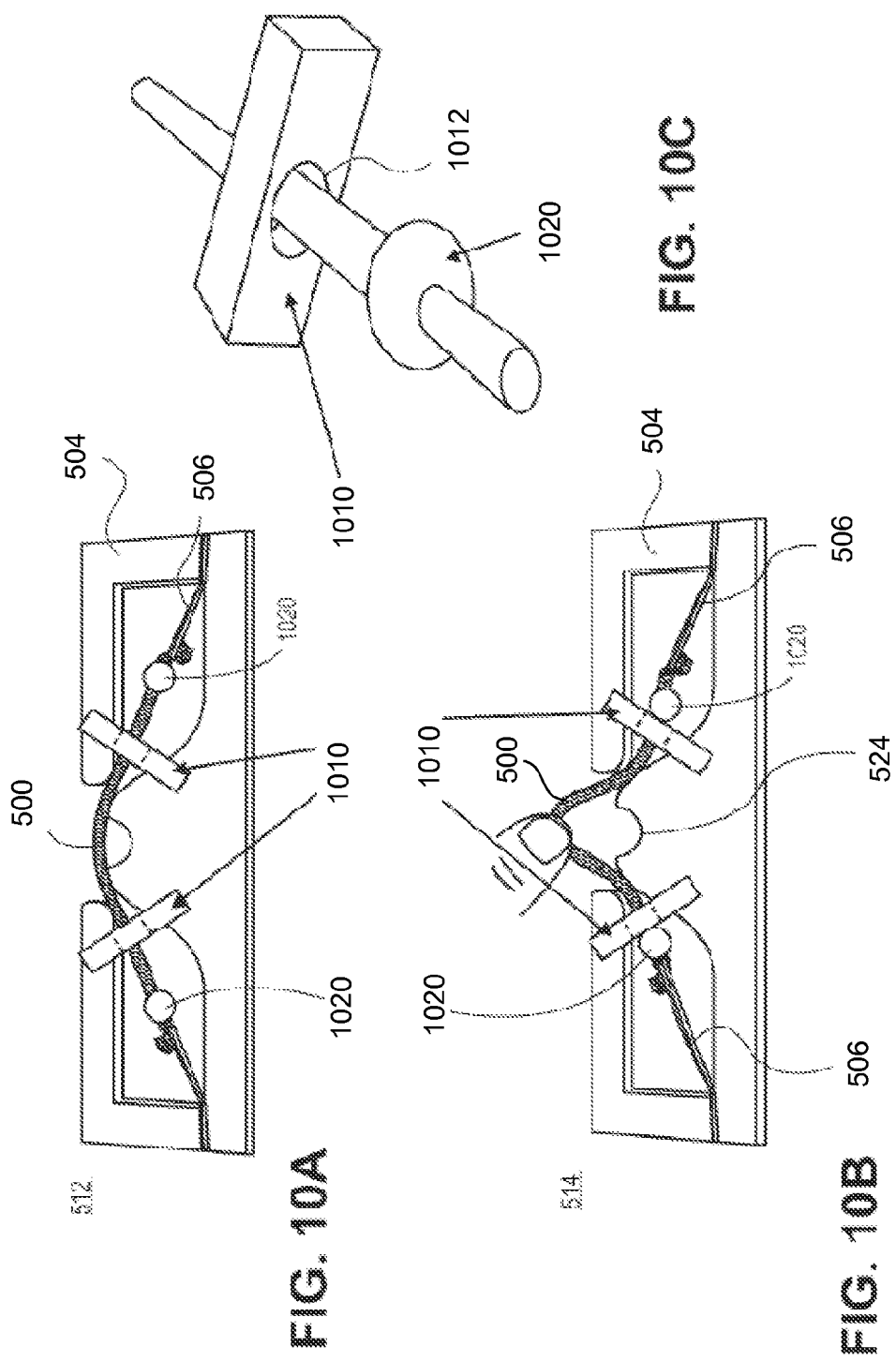

SELF-RETRACTING HANG TAB

BACKGROUND

Hang tabs are used to hang product packages on displays in stores. Hang tabs can be used to fit more products in the same space, and presenting the products in an easy-access form. Some hang tabs are made of sturdy plastic and pressure-sensitive adhesive that sticks to a surface of the package. Hang tabs generally have an opening or slot to receive one or more wire hangers, also referred to as pegs or wire pegs. There are a variety of display peg fixtures, such as single-wire or double-wire pegs. The hang tabs are generally adhered to the package they support. Some hang tabs are formed to fold flat against the package until the package is removed from a packaging case and hung for display. The hang tab can allow the product to be displayed vertically, face-forward anywhere in the store for maximum visibility, and can allow more products to be displayed in less space.

One conventional hang tab uses pressure-sensitive adhesive. These adhesives need to ensure that the hang tab is reliable in hanging a package for an indefinite amount of time. Some pressure-sensitive adhesive tabs have a folding plastic hang tab with extended legs for better adhesion. These pressure-sensitive adhesive hang tabs are static hang tabs. A drawback to adhesively attaching a hang tab to a product package is the fact that the hang tab is permanently fixed to the package, usually the exterior surfaces of the package. The adhesive portion is visible on the exterior of the package, potentially covering up package messaging and branding, as well as potentially causing an aesthetically displeasing look for potential customers. Also, the adhesive can start to peel, sheer, or rip off over time causing the hang tab to fail, and potentially damage the package for refitting with another hang tab. Another disadvantage may be that when not hanging, the hang tabs are still visible, such as when sitting on a shelf of the store.

Other conventional hang tabs are fixed or passive hang tabs, which when not in use or hanging, stand out and make the packaging less attractive. Some hang tabs have a built-in, folding plastic piece that is static. Another conventional hang tab is a deployable and retractable hang tab for articles. The hang tab is attached to the box after assembly of the box or from inside of the box before assembly of the box. The hang tab is restrained within a hand tab interface that is specially cut section of the package that provides a receptacle for attachment. The hang tab is designed so that when the hang tab is not in use, it can be partially or fully concealed within the box without falling into the box. This conventional hang tab does not self-retract and must be pushed/moved back into place, or, by chance, gravity may assist in helping retract the hang tab.

BRIEF DESCRIPTION OF THE DRAWINGS

The present invention will be understood more fully from the detailed description given below and from the accompanying drawings of various embodiments of the present invention, which, however, should not be taken to limit the present invention to the specific embodiments, but are for explanation and understanding only.

FIG. 1 illustrates a stack-up view of a slider hang tab according to one embodiment.

FIGS. 2A-2B are inside views of a product package having the slider hang tab of FIG. 1 according to one embodiment.

FIGS. 5A-5B illustrate a string hang tab in a retracted position and in a deployed position, respectively, according to another embodiment.

FIGS. 6A-6B illustrate inside views of a product package having an integrated slider-hang-tab assembly according to one embodiment.

FIGS. 8A-8B illustrate a self-retracting hang tab adhered to an external surface of a product package according to one embodiment.

FIGS. 10A-10B illustrate the string hang tab of FIGS. 5A-5B and load-holding bridges and stopping knots in a retracted position and in a deployed position, respectively, according to another embodiment.

FIG. 10C illustrates a close-up view of a load-holding bridge and stopping knot according to one embodiment.

DETAILED DESCRIPTION

Figure 3A:
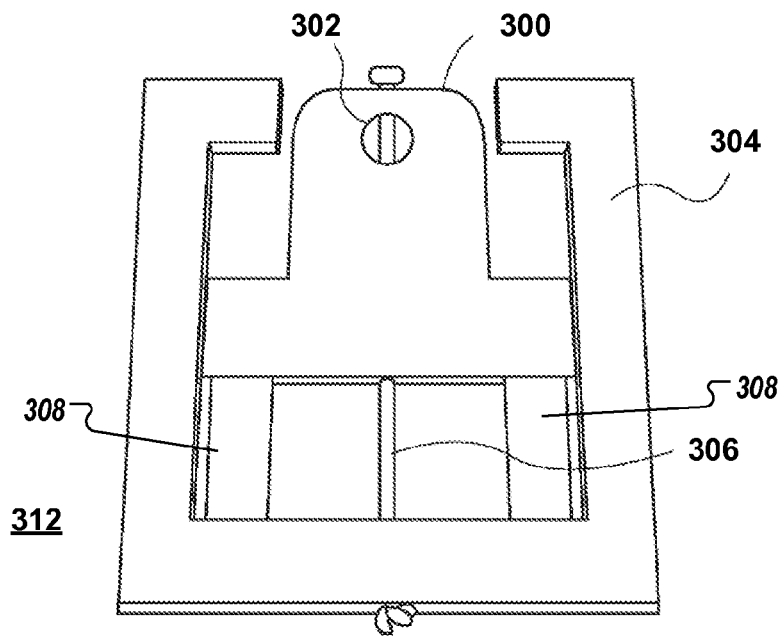
FIGS. 3A-3B illustrate a slider hang tab in a retracted position and in a deployed position, respectively, according to another embodiment.

Self-retracting hang tabs for product packages are described. Methods of manufacturing the self-retracting hang tabs are also described. One apparatus includes a frame, a biasing member coupled to the frame, and a hang tab disposed within the frame and coupled to the biasing member. The biasing member is configured to position the hang tab in a retracted position, at least partially out of view when attached to a product package. The biasing member is also configured to position the hang tab in a deployed position when the hang tab is under tension.

FIG. 1 illustrates a stack-up view of a slider hang tab according to one embodiment. The stack-up view shows a slider hang tab 100 disposed within a frame 104. The slider hang tab 100 is coupled to the frame by a biasing member 106. In one embodiment, the biasing member 106 is a spring. In another embodiment, the biasing member is an elastic band. Alternatively, other types of biasing members may be used, such as ties, tape, ribbons, straps or the like. These components are disposed between a first guide cover 108 and a second guide cover 110. The frame 104 has an opening 102 between the slide hang tab 100 and the product package 220. The opening 102 enables the product package 220 to be hung from a medium in the deployed position. For example, the opening 102 can receive a display peg to hang the product package in the deployed position. In the depicted embodiment, the opening 102 is a hole. In another embodiment, the opening 102 is an opening that forms a hook. Alternatively, other types of openings may be used to accommodate one or more display pegs. In one embodiment, the first guide cover 108 includes a finger hole 114 to allow a person to grab the slider hang tab 100. A pressure-sensitive adhesive release liner 112 is attached to the guide cover 110. The pressure-sensitive adhesive release liner 112 includes an adhesive layer and a liner, and when the liner is removed, the adhesive layer is exposed to allow the second guide cover 110 to be attached to a surface of a product package.

FIGS. 2A-2B are inside views of a product package 220 having the slider hang tab 100 of FIG. 1 according to one embodiment. The frame 104 is attached to the product package 220, such as by using an adhesive and guide covers as described above with respect to FIG. 1. Alternatively, the frame 104 can be coupled to the product package 220 in other ways as would be appreciated by one of ordinary skill in the art having the benefit of this disclosure. The biasing member 106 is coupled to the slider hang tab 100 and the frame 104. The frame 104 is configured to guide to the slider hang tab 100 and is configured to anchor the biasing member 106. The biasing member 106 is configured to retract the slider hang tab 100 into a retracted position when the slider hang tab 100 is not under tension and to allow the slider hang tab 100 to be in a deployed position when the slider hang tab 100 is under tension.

In the depicted embodiment, the slider hang tab 100 is configured to slide within the frame 104 between the retracted position (left) and the deployed position (right). The slider hang tab 100 includes a first portion and a second portion, the first portion being smaller than the second portion. The frame 104 includes a slot 122 that allows the first portion to slide out of the slot 122 and prevents the second portion from sliding out of the slot 122. Of course, other types of openings than slot 122 may be used, as well as other types of shapes for the slider hang tab 100 to prevent the slider hang tab 100 from being pulled out of the frame as would be appreciated by one of ordinary skill in the art having the benefit of this disclosure. In the depicted embodiment, the frame 104 has a U-shape with two stops to form the slot 122. In another embodiment, other shapes may be used for the slider hang tab 100 and the frame 104 as would be appreciated by one of ordinary skill in the art having the benefit of this disclosure.

The frame 104 guides the slider hang tab 100 and acts as an anchor for the biasing member 106. The frame 104 is disposed between the guide covers 108, 110 as described above with respect to FIG. 1. In another embodiment, the frame is considered the three pieces, including the frame 104, the guide covers 108, 110. In another embodiment, the frame may use a surface of the product package 220 as one of the guide cover. In this embodiment, an adhesive may be disposed on the frame 104 and the frame is attached directly to the surface of the product package 220. The biasing member 106 may be a spring or an elastic band that attaches to the slider hang tab 100 and the frame 104. In the natural state (FIG. 2A), also referred to as the retracted position, the slider hang tab 100 is retracted when the hang tab is not under tension. When under tension, the slider hang tab 100 slides to a deployed position (FIG. 2B).

Figure 3B:
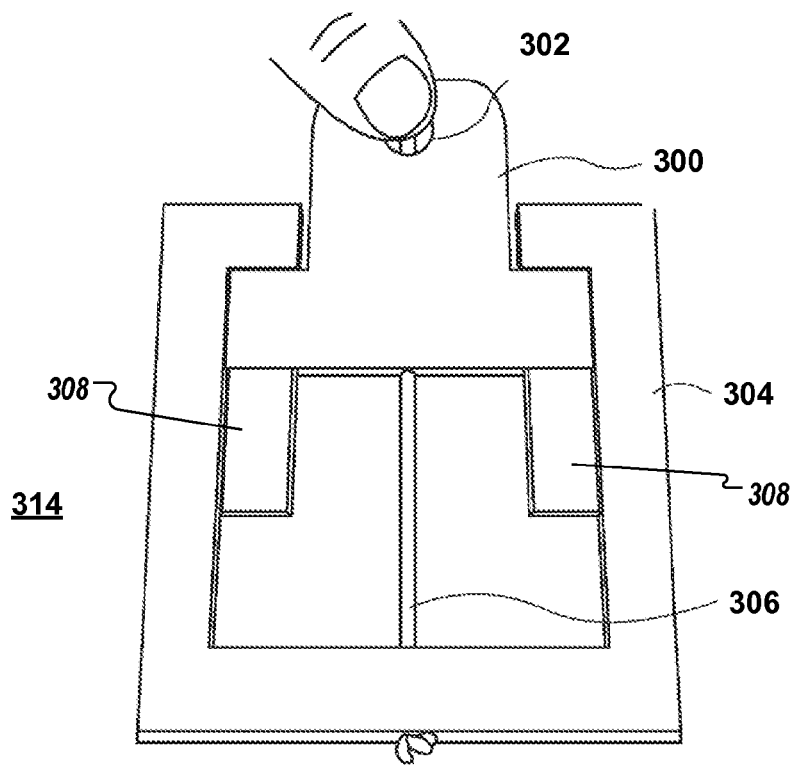

FIGS. 3A-3B illustrate a slider hang tab 300 in a retracted position 312 and in a deployed position 314, respectively, according to another embodiment. The slider hang tab 300 is similar to the slider hang tab 100 but includes two leg extensions 308 that extend substantially perpendicular to the second portion of the slider hang tab. This may allow a frame 304 to have a longer height dimension than the frame 104. In this embodiment, the frame 304 has a U-shape and two stops forming a slot through which only a portion of the slider hang tab 300 can pass. In the retracted position 312, the leg extensions rest against the bottom of the frame 304. The slider hang tab 300 is held in place by the frame 304 and the biasing member 306. The biasing member 306 may be a spring or an elastic band as described above. In this embodiment, the biasing member 306 is configured to position the slider hang tab 300 in the retracted position 312. The retracted position 312 may put the slider hang tab 300 out of view of the product package or at least partially out of view, as compared to the deployed position 314. The biasing member 306 is configured to position the slider hang tab 300 in the deployed position 314 when the slider hang tab 300 is under tension. For example, a person can grab the slider hang tab 300 and pull the slider hang tab 300 away from the product package and hang the slider hang tab on a display peg. The display peg can pass through an opening 302 of the slider hang tab 300. The display peg puts the slider hang tab 300 under tension, keeping the slider hang tab 300 in the deployed position 314. When the product package is removed from the display peg, the biasing member 306 retracts the slider hang tab 300 from the deployed position 314 to the retracted position 312. Alternatively, the product package can be hung from other mediums as would be appreciated by one of ordinary skill in the art having the benefit of this disclosure.

Figure 4A:
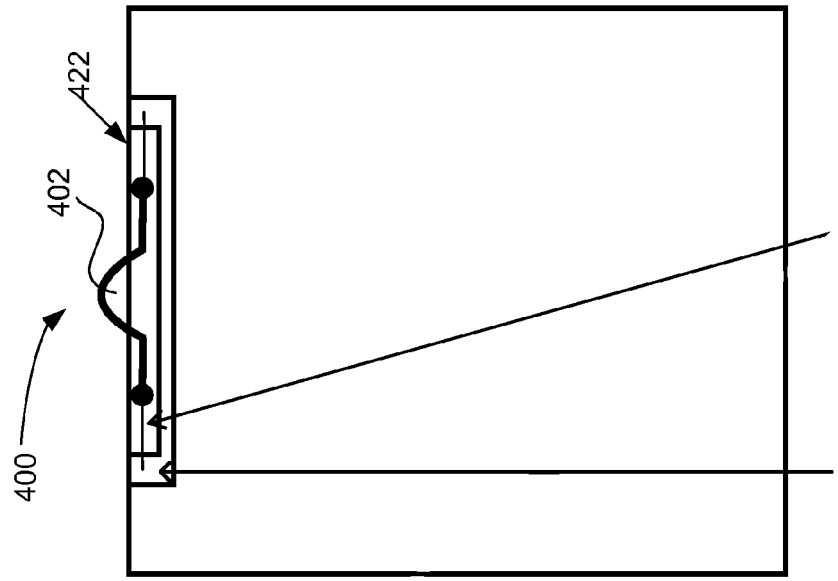
FIGS. 4A-4B are inside views of a product package having a string hang tab according to one embodiment.
Figure 4B:
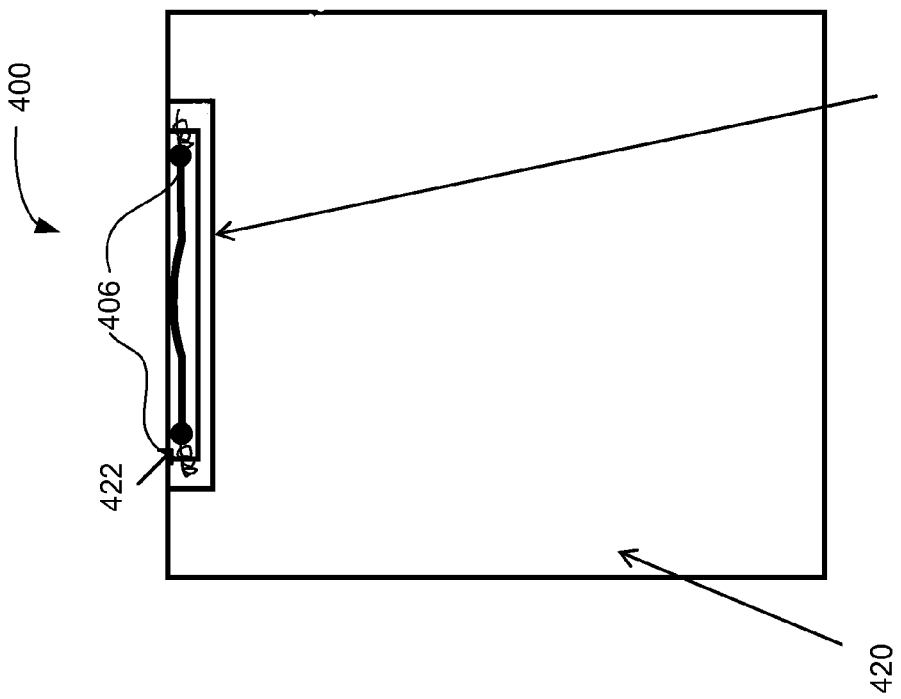

FIGS. 4A-4B are inside views of a product package 420 having a string hang tab 400 according to one embodiment. The frame 404 is attached to the product package 420, such as by using an adhesive as described herein. The biasing member 406 is coupled to the string hang tab 400 and the frame 404. The frame 404 is configured to guide to the string hang tab 400 and is configured to anchor the biasing member 406. The biasing member 406 is configured to retract the string hang tab 400 into a retracted position when the string hang tab 400 is not under tension and to allow the string hang tab 400 to be in a deployed position when the string hang tab 400 is under tension.

In the depicted embodiment, the string hang tab 100 is configured to extend and retract to and from the retracted position (FIG. 4A) and the deployed position slide (FIG. 4B) within the frame 404. The frame 404 includes a slot 422 that allows the string hang tab 400 to extend out from the product package 420 to form an opening 402 between the string hang tab 400 and the product package 420. The opening 402 can receive a display peg to hang the product package in the deployed position. Load-holding bridges and knots or beads can be used to prevent the string hang tab 400 from extending too far out of the product package, as described below with respect to FIGS. 10A-10C. Of course, other types of openings than slot 422 may be used, as well as other types of mechanisms may be used to prevent the string hang tab 400 from being pulled out of the frame 404 as would be appreciated by one of ordinary skill in the art having the benefit of this disclosure. Alternatively, the opening 402 can enable the product package to be hung from other mediums.

The frame 404 guides the string hang tab 400 and acts as an anchor for the biasing member 406. The frame 404 may be disposed between one or more guide covers as described herein. The string hang tab 400 includes a string configured to retract from the deployed position and to extend to the deployed position when under tension. The string forms the opening 402 between the string and the product package 420. As described above, the opening 402 is configured to receive a display peg to hang the product package in the deployed position. The biasing member 406 may be a spring or an elastic band that attaches to each end of the string hang tab 400 and the frame 404. In one embodiment, the biasing member 406 includes a first spring or elastic band coupled to a first end of the string and a second spring or elastic band coupled to a second end of the string. In the natural state (FIG. 4A), also referred to as the retracted position, the string hang tab 400 is retracted when the string hang tab 400 is not under tension. When under tension, the string hang tab 400 extends to a deployed position (FIG. 4B).

FIGS. 5A-5B illustrate a string hang tab 500 in a retracted position 512 and in a deployed position 514, respectively, according to another embodiment. The string hang tab 500 is similar to the string hang tab 400 but includes a positioning structure to position at the retracted position. The positioning structure can be used to enable the string hang tab 400 to be grabbed by a user while in the retracted position. In this embodiment, the frame 504 has an outer structure that has a substantially rectangular shape with an opening through which the string passes. The positioning structure is positioned at the center of the bottom portion of the rectangle and extends towards the opening. This retracted position can be used to position the string towards the opening through which the string passes. The positioning structure can be used to keep the string from falling out of reach of a user. For example, the positioning structure can be used to position the string at a location for a user to grab the string. In the depicted embodiment, the positioning structure has a notch 524 to allow the user to grab the string with greater ease than without the notice 524. In this embodiment, the positioning structure is part of the frame 504. In another embodiment, the positioning structure is a separate structure from the frame 504. In other embodiments, other shapes may be used for the frame 504 as would be appreciated by one of ordinary skill in the art having the benefit of this disclosure.

In the retracted position 512, the string is held in rest against the positioning structure by the biasing member 506. The biasing member 506 may be a spring or an elastic band as described above. In this embodiment, the biasing member 506 is configured to position the string hang tab 500 in the retracted position 512. The retracted position 512 may put the string hang tab 500 out of view of the product package or at least partially out of view, as compared to the deployed position 514. The biasing member 506 is configured to position the string hang tab 500 in the deployed position 514 when the string hang tab 500 is under tension. For example, a person can grab the string hang tab 500 and pull the string hang tab 500 away from the product package and hang the string hang tab 500 on a display peg or other mediums. The display peg can pass through the opening between the string hang tab 500 and the product package. The display peg puts the string hang tab 500 under tension, keeping the string hang tab 500 in the deployed position 514. When the product package is removed from the display peg, the biasing member 306 retracts the string hang tab 500 from the deployed position 514 to the retracted position 512.

FIGS. 6A-6B illustrate inside views of a product package 620 having an integrated slider-hang-tab assembly 600 according to one embodiment. In this embodiment, the slider-hang-tab assembly 600 includes a slider hang tab 602, a frame 604 and a biasing member 606 substantially in the form of an integrated component. For example, the slider-hang-tab assembly 600 can be a material die cut or a molded piece of material. The hang tab 602 includes a first opening 608 configured to receive a display peg to hang the product package 620 in the deployed position. The slider-hang-tab assembly 600 is attached to the product package 620, such as by using an adhesive and guide covers as described above with respect to FIG. 1. Alternatively, the slider-hang-tab assembly 600 can be coupled to the product package 620 in other ways as would be appreciated by one of ordinary skill in the art having the benefit of this disclosure. The frame 604 is configured to guide to the slider-hang-tab assembly 600 and is configured to anchor the biasing member 606. The biasing member 606 is configured to retract the slider-hang-tab assembly 600 into a retracted position when the slider-hang-tab assembly 600 is not under tension and to allow the slider-hang-tab assembly 600 to be in a deployed position when the slider-hang-tab assembly 600 is under tension.

In the depicted embodiment, the slider hang tab 602 is configured to slide within the frame 604 between the retracted position (FIG. 6A) and the deployed position (FIG. 6B). The slider hang tab 602 includes a first portion and a second portion, the first portion being smaller than the second portion. The frame 604 includes a slot 622 that allows the first portion to slide out of the slot 622 and prevents the second portion from sliding out of the slot 622. Of course, other types of openings than slot 622 may be used, as well as other types of shapes for the slider hang tab 602 to prevent the slider hang tab 602 from being pulled out of the frame 604 as would be appreciated by one of ordinary skill in the art having the benefit of this disclosure. In the depicted embodiment, the frame 604 has a U-shape with two stops to form the slot 622. In another embodiment, other shapes may be used for the slider hang tab 602 and the frame 604 as would be appreciated by one of ordinary skill in the art having the benefit of this disclosure.

The frame 604 guides the slider hang tab 602 and acts as an anchor for the biasing member 606. In one embodiment, the frame 604 is disposed between the guide covers 108, 110 as described above with respect to FIG. 1. In another embodiment, the slider-hang-tab assembly 600 can be an integrated component with the guide covers. In these embodiments, instead of the biasing member 606 being a separate spring or elastic band, the slider-hang-tab assembly 600 may include a spring member as part of the assembly for the biasing member 606. In the natural state (FIG. 6A), also referred to as the retracted position, the slider hang tab 602 is retracted when the slider hang tab 602 is not under tension. When under tension, the slider hang tab 602 slides to a deployed position (FIG. 6B).

Figure 7A:
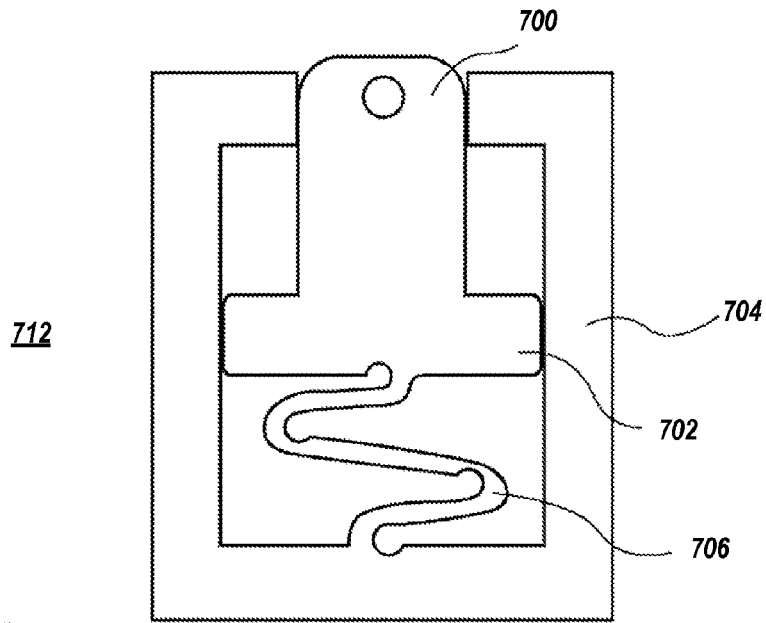
FIGS. 7A-7B illustrate an integrated slider-hang-tab assembly in a retracted position and in a deployed position, respectively, according to another embodiment.
Figure 7B:
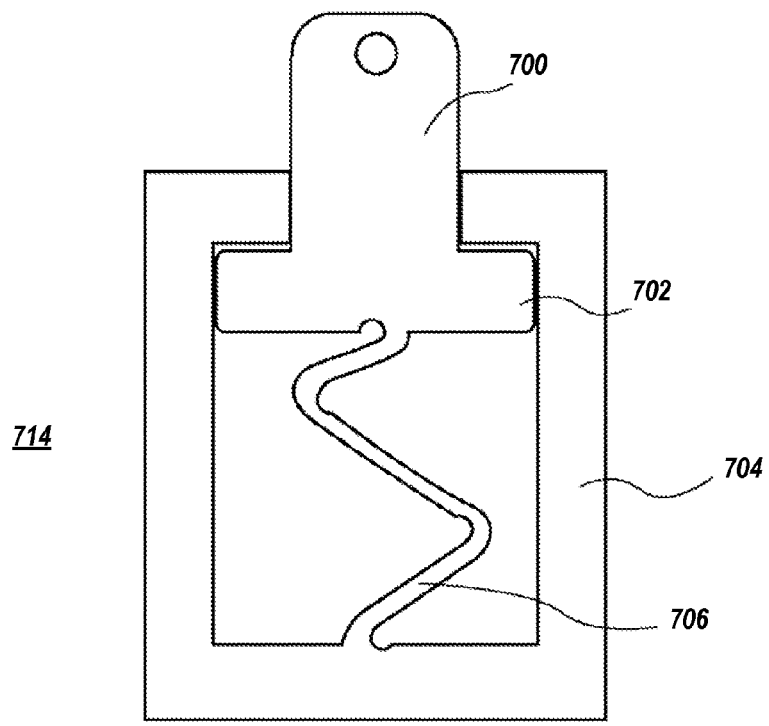

FIGS. 7A-7B illustrate an integrated slider-hang-tab assembly 700 in a retracted position 712 and in a deployed position 714, respectively, according to another embodiment. The integrated slider-hang-tab assembly 700 is similar to the integrated slider-hang-tab assembly 600, and includes a slider hang tab 702, a frame 704 and a biasing member 706. In this embodiment, the frame 704 has a U-shape and two stops forming a slot through which only a portion of the slider hang tab 702 can pass. In the retracted position 712, the slider hang tab 702 is held in place by the frame 704 and the biasing member 706. The biasing member 706 is configured to position the slider hang tab 702 in the retracted position 712. The retracted position 712 may put the slider hang tab 702 out of view of the product package or at least partially out of view, as compared to the deployed position 714. The biasing member 706 is configured to position the slider hang tab 702 in the deployed position 714 when the slider hang tab 702 is under tension. For example, a person can grab the slider hang tab 702 and pull the slider hang tab 702 away from the product package and hang the slider hang tab 702 on a display peg or other medium. The display peg can pass through an opening of the slider hang tab 702. The display peg puts the slider hang tab 702 under tension, keeping the slider hang tab 702 in the deployed position 714. When the product package is removed from the display peg, the biasing member 706 retracts the slider hang tab 702 from the deployed position 714 to the retracted position 712. The biasing member 706 may be a spring member or other shapes or forms that retracts back to the retracted position 712 when not under tension and extends to the deployed position 714 when under tension.

FIGS. 8A-8B illustrate a self-retracting hang tab 800 adhered to an external surface 804 of a product package 820 according to one embodiment. In this embodiment, the self-retracting hang tab 800 includes an adhesive 802 on a backside of the assembly that is attached to the external surface 804 of the product package 820. In one embodiment, the adhesive 802 is a pressure-sensitive adhesive coupled to one of the surfaces of the self-retracting hang tab 800. For example, a pressure-sensitive adhesive release liner can be attached to a guide cover of the self-retracting hang tab 800. When the release liner is removed, the adhesive 802 is exposed to adhere to the external surface 804.

Figure 9B:
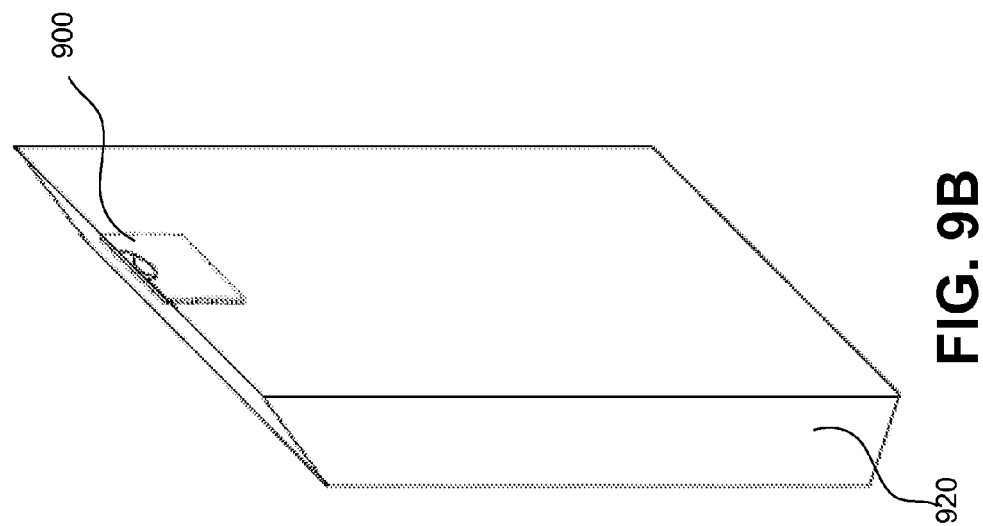
FIGS. 9A-9B illustrate a self-retracting hang tab adhered to an internal surface of a product package according to one embodiment.
Figure 9A:
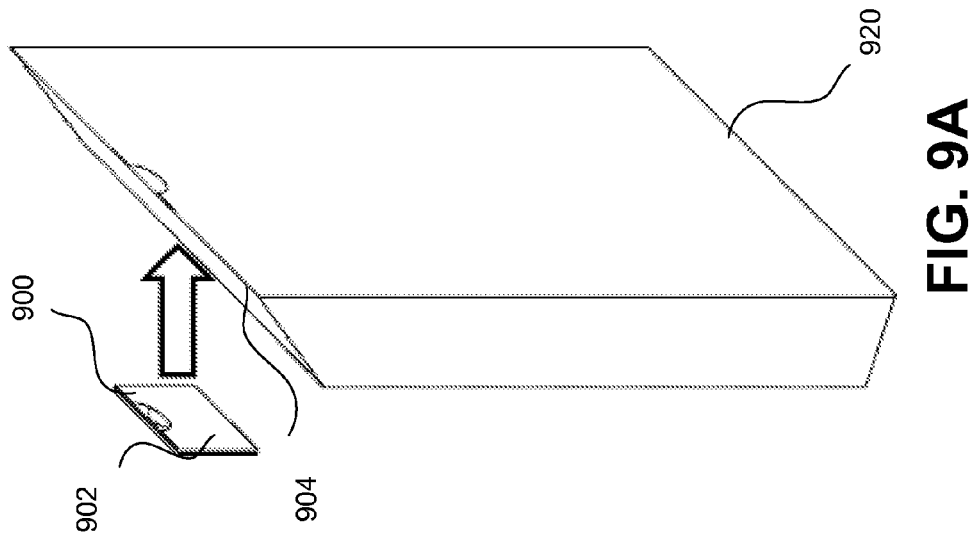

FIGS. 9A-9B illustrate a self-retracting hang tab 900 adhered to an internal surface 904 of a product package 920 according to one embodiment. In this embodiment, the self-retracting hang tab 900 includes an adhesive 902 on a front side of the assembly that is attached to the internal surface 904 of the product package 920. In one embodiment, the adhesive 902 is a pressure-sensitive adhesive coupled to one of the surfaces of the self-retracting hang tab 900. Like, above, a pressure-sensitive adhesive release liner can be attached to a guide cover of the self-retracting hang tab 900. When the release liner is removed, the adhesive 902 is exposed to adhere to the internal surface 904. This can be done to hide the self-retracting hang tab 900 from view on the external surfaces of the product package 920.

FIGS. 10A-10B illustrate the string hang tab of FIGS. 5A-5B and load-holding bridges and stopping knots in a retracted position and in a deployed position, respectively, according to another embodiment. FIG. 10C illustrates a close-up view of a load-holding bridge and stopping knot according to one embodiment. In this embodiment, a pair of load-holding bridges 1010 is disposed on the frame 504. For example, as depicted, one side of one of the load-holding bridges is attached to the frame 504 and the other side to the positioning structure. The other load-holding bride is attached between the frame 504 on the other side of the opening of the frame 504 and the positioning structure. The string hang tab 500 includes a pair of stopping knots or beads 1020. The load-holding bridges each includes an opening 1012 (e.g., hole) through which the string passes but stops at the respective one of the pair of stopping knots or beads 1020, as illustrated in FIG. 10C.

Figure 11:
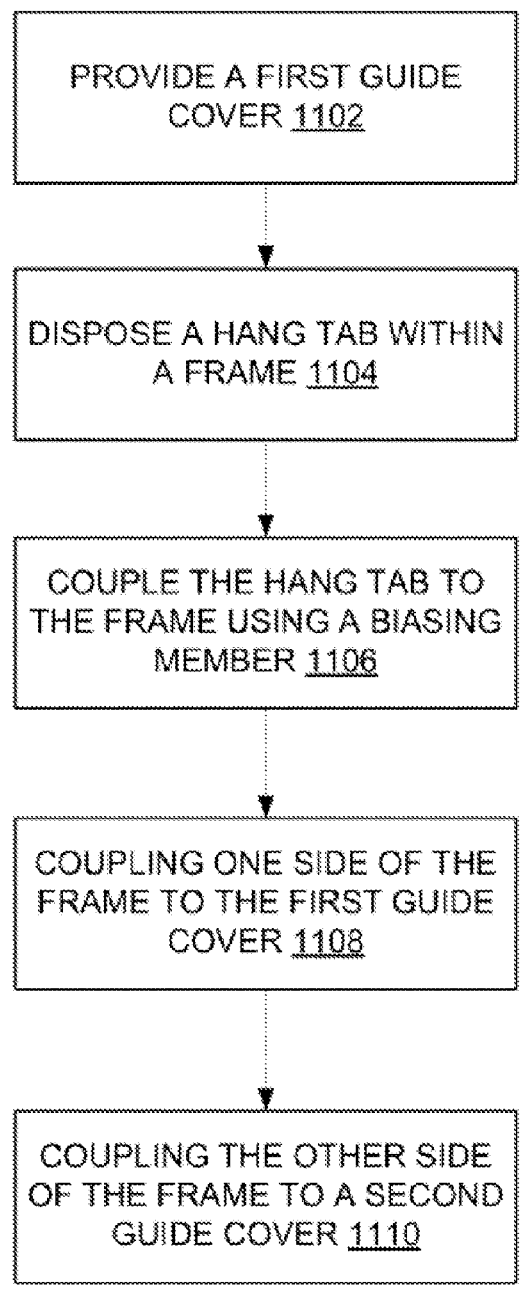

FIG. 11 is a flow diagram of an embodiment of a method 1100 of manufacturing a self-retracting hang tab for a product package. The method 1100 includes providing a first guide cover (block 1102). A hang tab (any of the self-retracting hang tabs described herein) is disposed within a frame (block 1104) and the hang tab is coupled to the frame using a biasing member (block 1106). One side of the frame is coupled to the first guide cover (block 1108), and the other side of the frame is coupled to a second guide cover (block 1108). The hang tab, biasing member and frame are disposed between the first guide cover and the second guide cover. As describe herein, the biasing member is configured to position the hang tab in a retracted position and to position the hang tab in a deployed position when the hang tab is under tension.

In yet a further embodiment, a pressure-sensitive adhesive release liner is coupled to an external surface of the second guide cover. A release liner of the pressure-sensitive release linear is removed to expose an adhesive of the pressure-sensitive adhesive release liner. The second guide cover is attached to a surface of the product package using the exposed adhesive. The surface may be an external surface of the product package or an internal surface of the product package.

In one embodiment, the product package is used for a user device. The user device may be any content rendering device that includes a wireless modem for connecting the user device to a network. Examples of such user devices include electronic book readers, cellular telephones, personal digital assistants (PDAs), portable media players, tablet computers, netbooks and the like. Alternatively, the product package may be used for other items as would be appreciated by one of ordinary skill in the art having the benefit of this disclosure.

In the above description, numerous details are set forth. It will be apparent, however, to one of ordinary skill in the art having the benefit of this disclosure, that embodiments of the present invention may be practiced without these specific details. In some instances, well-known structures and devices are shown in block diagram form, rather than in detail, in order to avoid obscuring the description.

It should also be noted that the terms "when" or the phrase "in response to," as used herein, should be understood to indicate that there may be intervening time, intervening events, or both before the identified operation is performed.

It is to be understood that the above description is intended to be illustrative, and not restrictive. Many other embodiments will be apparent to those of skill in the art upon reading and understanding the above description. The scope of the present invention should, therefore, be determined with reference to the appended claims, along with the full scope of equivalents to which such claims are entitled.

What is claimed is:

1. A hang tab assembly for a product package, the hang tab assembly comprising:
   a self-retracting hang tab to be secured to the product package to allow the product package to be hung, wherein the self-retracting hang tab comprises a first portion and a second portion, the first portion being smaller than the second portion;
   a frame constituting at least a portion of a housing of the hang tab, the frame to be secured to a surface of the product package and to guide the self-retracting hang tab when moving between a retracted position and a deployed position, wherein the frame has a frame opening that allows the first portion to slide out of the frame opening and prevents the second portion from sliding out of the frame opening; and
   a biasing member coupled to the self-retracting hang tab and the frame, wherein the biasing member is configured to retract the self-retracting hang tab into the retracted position when the self-retracting hang tab is not under tension and to allow the self-retracting hang tab to be in the deployed position when the self-retracting hang tab is under tension, wherein the self-retracting hang tab comprises two leg extensions substantially perpendicular to the second portion with the two leg extensions resting on a bottom of the frame in the retracted position.

2. The hang tab assembly of claim 1, further comprising:
   a second guide cover disposed on a first side of the frame, the second guide cover to be secured to the surface of the product package; and
   a first guide cover disposed on a second side of the frame, wherein the frame, biasing member, and self-retracting hang tab are disposed between the second guide cover and the first guide cover.

3. The hang tab assembly of claim 2, further comprising a liner coupled to the second guide cover, wherein the liner comprises an adhesive to secure the second guide cover to the product package.

4. The hang tab assembly of claim 1, wherein the self-retracting hang tab comprises a slider hang tab configured to slide within the frame between the retracted position and the deployed position, wherein the biasing member comprises at least one of a spring or an elastic coupled to the slider hang tab, and wherein the slider hang tab comprises a first opening enabling the product package to be hung from a medium in the deployed position.

5. An apparatus comprising:
a frame to at least partially house a slider hang tab, the slider hang tab to enable a product package to be hung from a medium in a deployed position;
a biasing member integrally formed with the frame, the biasing member to retract the slider hang tab from the deployed position to a retracted position when the slider hang tab is not under tension; and
the slider hang tab disposed within the frame and integrally formed with the biasing member, wherein the slider hang tab comprises:
a tab opening to enable the product package to be hung in the deployed position;
a first portion; and
a second portion, the first portion being smaller than the second portion, and wherein the frame has a U-shape with two stops to form a frame opening that allows the first portion to slide out of the frame opening and prevents the second portion from sliding out of the frame opening.

6. The apparatus of claim 5, further comprising:
a second guide cover disposed on a first side of the frame, the second guide cover to be secured to a surface of the product package; and
a first guide cover disposed on a second side of the frame, wherein the frame, biasing member, and slider hang tab are disposed between the second guide cover and the first guide cover.

7. The apparatus of claim 6, further comprising an adhesive layer coupled to the second guide cover and configured to attach the second guide cover to an external surface of the product package.

8. The apparatus of claim 6, further comprising an adhesive layer coupled to the second guide cover and configured to attach the second guide cover to an internal surface of the product package.

9. A method of manufacturing a self-retracting hang tab for a product package, the method comprising:
providing a first guide cover;
disposing a hang tab within a frame, the hang tab enabling the product package to be hung from a medium in a deployed position, wherein the hang tab comprises a first portion and a second portion, the first portion being smaller than the second portion, wherein the frame has a frame opening that allows the first portion to slide out of the frame opening and prevents the second portion from sliding out of the frame opening, wherein the hang tab comprises two leg extensions substantially perpendicular to the second portion with the two leg extensions resting on a bottom of the frame in a retracted position;
coupling the hang tab to the frame at least in part using a biasing member, the biasing member to retract the hang tab when the hang tab is not under tension;
coupling the first guide cover to one side of the frame; and
coupling a second guide cover to another side of the frame, wherein the hang tab, biasing member, and frame are disposed between the first guide cover and the second guide cover, and wherein the biasing member is to move the hang tab from the deployed position to the retracted position when not under tension, the deployed position being when the product package is at least partially suspended from a medium using the hang tab.

10. The method of claim 9, further comprising coupling an adhesive liner on an external surface of the second guide cover.

11. The method of claim 10, further comprising:
removing a release liner of the adhesive liner to expose an adhesive of the adhesive liner; and
attaching the second guide cover to an external surface of the product package.

12. The method of claim 10, further comprising:
removing a release liner of the adhesive liner to expose an adhesive of the adhesive liner; and
attaching the second guide cover to an internal surface of the product package.

* * * * *